(12) United States Patent
Mátyus et al.

(10) Patent No.: US 6,248,907 B1
(45) Date of Patent: Jun. 19, 2001

(54) N-([1,4]BENZODIOXAN-2-YLMETHYL)-N-(3-CHLORO-1-PROPYL)-AMINE

(75) Inventors: Péter Mátyus; László Hársing; Marianne Tapfer née Karim; Judit Kosáry; Ágnes Papp née Behr; Antal Simay; Yemane Tilahun; Éva Tomori née Joszt; Edit Horváth; Katalin Horváth; Ildikó Varga; Erzsébet Zára née Kaczián; Margit Bidló née Iglóy; Alice Druga; György Rabloczky; Márta Varga; Egon Kárpáti; Endre Kasztreiner; István Király; Ildikó Máthé née Gyóry; György Máthé; László Sebestyén, all of Budapest; Nándor Makk, Kismaros, all of (HU)

(73) Assignee: Gyogyszerkutato Intezet Kft., Budapest (HU)

( * ) Notice: Subject to any disclaimer, the term of this patent is extended or adjusted under 35 U.S.C. 154(b) by 0 days.

(21) Appl. No.: 09/649,077

(22) Filed: Aug. 28, 2000

Related U.S. Application Data

(62) Division of application No. 08/973,584, filed as application No. PCT/HU96/00030 on May 28, 1996.

(30) Foreign Application Priority Data

May 29, 1995 (HU) .................................................. 9501560

(51) Int. Cl.⁷ ................................................. C07D 319/14
(52) U.S. Cl. ........................................................ 549/366
(58) Field of Search ............................................... 549/366

*Primary Examiner*—Amelia Owens
(74) *Attorney, Agent, or Firm*—Keil & Weinkauf

(57) ABSTRACT

The invention relates to R-2-[3-([1,4]benzodioxan-2-ylmethylamino)-1-propyl]-3(2H)-pyridazinone of formula (1), and to S-2-[3-([1,4]benzodioxan-2-ylmethylamino)-1-propyl]-3(2H)-pyridazinone of formula (2), and to acid-addition salts thereof as well as pharmaceutical compositions containing these compounds. Furthermore, the invention relates to a process for the preparation of the above compounds. The new starting compounds of formulae (4) and (5) are also involved in the scope of the invention. The compounds according to the invention possess $\alpha_1$- and $\alpha_2$-adrenoceptor antagonistic effects and urogenital selectivity. Thus, they are useful for the treatment of the benign prostate hyperplasia.

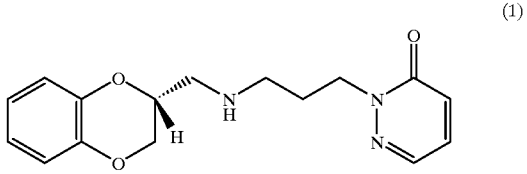

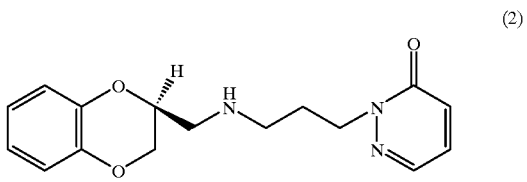

4 Claims, No Drawings

N-([1,4]BENZODIOXAN-2-YLMETHYL)-N-(3-CHLORO-1-PROPYL)-AMINE

This invention is a Division of Ser. No. 08/973,584 filed Jul. 20, 1998 which is a 371 of PCT/4496/00030, filed Mar. 28, 1996.

The invention relates to the compounds R-2-[3-([1,4]benzodioxan-2-ylmethylamino)-1-propyl]-3(2H)-pyridazinone of formula (1)

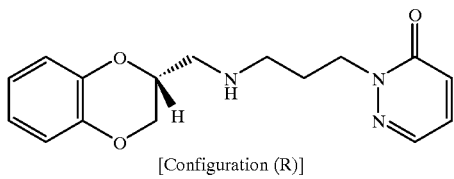

(1)

[Configuration (R)]

and S-2-[3-)[1,4]benzodioxan-2-ylmethylamino)-1-propyl]-3(2H)-pyridazinone of formula (2)

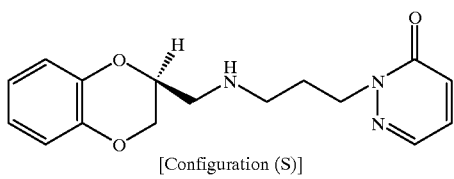

(2)

[Configuration (S)]

as well as their acid-addition salts. The invention relates also to pharmaceutical compositions containing these compounds as well as to a process for the preparation of these compounds.

Antihypertensive 2-(aminoalkyl)-3(2H)-pyridazinone derivatives are published in the Hungarian patent specification No. 195,645. A typical example of these substances is 2-[3-([1,4]benzodioxan-2-ylmethylamino)-1-propyl]-3(2H)-pyridazinone of formula (3),

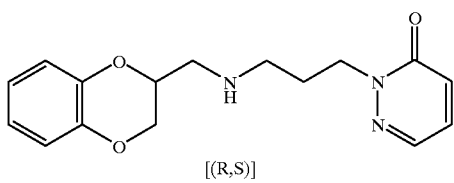

(3)

[(R,S)]

i.e. racemic form of the compounds of formulae (1) and (2), a very low dose of which significantly decreases the arterial blood pressure in animal experiments under in vivo conditions. According to the description, these pyridazinone derivatives selectively inhibit $\alpha_1$-adrenoceptors and possess a calcium antagonistic effect. Thus, they meet the demands of a multicomponent antihypertensive action; no comments are made about any other possible pharmacological effects of these compounds.

Recently, the possibilities of drug treatment of benign prostatic hypertrophy (hereinafter abbreviated: BPH; the benign tissue hyperplasia of the prostate). Till now, a surgical intervention has nearly exclusively been performed to overcome this disorder affecting about 50% of men above 50 years. Due to the higher risk in the elderly and high costs of surgical intervention, drug therapy has called an increased attention.

It has been stated that a major part of symptoms accompanying BPH are related to an increased tone of the smooth muscles of the prostatic zone or urethra and the bladder neck, which leads to an increase in the intraurethral pressure. Furthermore, it has been proven that in these tissues the smooth musculature, having an $\alpha$-adrenergic innervation containing both $\alpha_1$- and $\alpha_1$-adrenoceptors, can be relaxed by $\alpha$-adrenergic blocking agents. Thus, the symptoms of BPH can be favourably influenced by $\alpha$-adrenergic blocking drugs [see, e.g.: E. Shapiro et al.: J. Urol. 137, 565 (1987); H. Lepor, J. Androl. 12, 356 (1991); as well as S. Heda et al.: Eur. J. Pharm. 103, 249 (1994). However, for the treatment of BPH, such ($\alpha$-adrenoceptor blocking compounds can only be taken preferably into account, which do not exert any considerable cardiovascular side effects, e.g. a decrease in blood pressure, orthostatic hypotension or syncope.

Due to the inhibition of presynaptic $\alpha_2$-receptors by using nonselective $\alpha_1$- and $\alpha_2$-adrenoceptor blocking agents, other side effects could also appear (e.g. the heart rate is increased). Therefore, exclusively $\alpha_1$-adrenoceptor blocking drugs are therapeutically employed at present.

Conclusively, the urogenital selectivity of the active agents, i.e. its selectivity for the prostate-urethra-bladder system is a very important requirement; nevertheless, the selectivity of available drugs (e.g. prazosin, terazosin, alfuzosin) is low or moderate and as a consequence, they show adverse effects. Thus novel urogenitally selective $\alpha$-adrenoceptor blocking agents are really needed, which are able to favourably influence the symptoms of BPH and are free of untoward side effects.

During our investigations it has been surprisingly found that the $\alpha$-adrenoceptor blocking compounds of formulae (1) and (2) of the invention also have a significant urogenital selectivity; while these compounds diminish the intraurethral pressure at very low doses, they simultaneously exhibit a very weak influence only on other cardiovascular parameters. Thus, they meet the above requirements.

The efficacy and selectivity of the compounds were proven under in vivo conditions as well as by in vitro experiments on isolated organs and receptor-binding assays.

In an in vivo animal model, in anaesthetized cat, intraurethral hypertension can be induced by $\alpha_1$-adrenoceptor agonists [e.g. phenylephrine, which is chemically (−)-1-(3-hydroxyphenyl)-2-(methylamino)ethanol]. This hypertension-inducing effect can be antagonized by $\alpha_1$-adrenoceptor antagonists. The antihypertensive effect is expressed by reduction of the diastolic pressure. Results of this experiment are summarized in Table 1 (the experiment is described in detail in the Pharmacological part).

TABLE 1

Effects of compounds of formulae (1) and (2) on phenylephrine-induced intraurethral hypertension and diastolic pressure, respectively

| | $ED_{50}$ ($\mu$g/kg, iv.) | | |
|---|---|---|---|
| Compound | urethra[a] | diastolic pressure[b] | D/U[c] |
| (1) | 13.9 | >888 | >63.9 |
| (2) | 3.4 | 90 | 26.5 |

TABLE 1-continued

Effects of compounds of formulae (1) and (2) on phenyl-
ephrine-induced intraurethral hypertension and diastolic
pressure, respectively

| | $ED_{50}$ ($\mu$g/kg, iv.) | | |
|---|---|---|---|
| Compound | urethra[a] | diastolic pressure[b] | D/U[c] |
| (3) | 28.4 | 130 | 4.6 |
| Prazosin | 18.7 | 25 | 1.3 |

Remarks:
[a]: Dose decreasing by 50% the hypertension induced by a 15 $\mu$g/kg/min intravenous dose of phenylephrine
[b]: Dose decreasing by 50% the diastolic total pressure increased by phenylephrine
[c]: $ED_{50}$ (diastolic pressure)/$ED_{50}$ (urethra)

It is obvious from the above data that the intraurethral pressure-decreasing effects of compounds of formulae (1) and (2) of the invention appear in a low dose; moreover their urogenital selectivity (expressed as D/U) considerably exceeds the selectivity of the racemic compound of formula (3) and that of prazosin.

In addition, investigations were performed on blood vessel and human hyperplasic prostate tissue preparations. In these experiments, a mesenteric artery was used as a model of resistance vessels which affect the blood pressure. We measured the extent of inhibition of the compounds of the invention and that of the reference drugs, respectively, on the contraction-inducing action of the $\alpha_1$-agonist (phenylephrine). The $\alpha_1$-adrenoceptor antagonism was then characterized by $pA_2$ values. The results are shown in Table 2.

TABLE 2

Evaluation of $\alpha_1$-adrenoceptor antagonistic effect in isolated organ experiments

| | $pA^2$ | | |
|---|---|---|---|
| Compound | rat mesenteric artery | human hyperplasic prostate tissue | Selectivity[a] (prostate/ /artery) |
| (1) | 6.56 | 7.20 | 4.37 |
| (2) | 7.68 | 8.23 | 3.55 |
| (3) | 7.16 | 7.51 | 2.24 |
| Alfuzosin | 3.60 | 8.01 | 0.26 |
| Terazosin | 8.45 | 8.39 | 0.87 |

Remark:
[a]: Antilogarithmic ratio of $pA_2$ value

The data of Table 2 show that the compounds of formulae (1) and (2) possess a strong $\alpha_1$-adrenoceptor antagonistic effect, which is more pronounced on the prostate tissue than on the resistance artery preparation. It is also remarkable that the prostate selectivity of the compounds according to the invention is more favourable than that of any reference drugs including the racemic compound of formula (3).

As mentioned above, an $\alpha_2$-adrenoceptor blocking component may also be of importance in treatment of BPH if inhibition of the postsynaptic $\alpha_2$-adrenoceptors is more pronounced than that of presynaptic $\alpha_2$-receptors Moreover, as shown more recently, $\alpha_2$-antagonists, besides their capacity of reducing the overactivity of sympathetic control in the prostate, may be able to effectively reduce hormonally induced prostatic stiffness [see, in R. R. Ruffolo et al.: Eur. J. Med. Chem., 30S, 269 (1995)].

The pre- and post-synaptic $\alpha_2$-adrenoceptor antagonistic effects of the compounds according to the invention were determined on rat vas deferens and dog vena saphena preparations by using xylazine [chemically 5,6-dihydro-2-(2,6-dimethylphenylamino)-1,3-thiazine] or UK 14304 [chemically 5-bromo-6-(2-imidazolin-2-ylamino) quinoxaline] as agonists. The antagonism was characterized by the $pA_2$ values The results are summarized in Table 3.

TABLE 3

Pre- and postsynaptic $\alpha_2$-adrenoceptor antagonistic effects on vas deferens and vena saphena preparations

| | $pA_2$ | | Selectivity[a] postsynaptic/ presynaptic |
|---|---|---|---|
| Compound | presynaptic | postsynaptic | |
| (1) | 5.81 | 7.87 | 115.0 |
| (2) | 6.81 | 8.14 | 21.4 |
| Yohimbine | 6.93 | 8.05 | 13.2 |

Remark:
[a]: Antilogarithmic ratio of $pA_2$ values

On the basis of the above data it can be stated that both compounds of formulae (1) and (2) do have a strong $\alpha_2$-adrenoceptor antagonistic activity and, surprisingly, they exert an excellent selectivity toward the postsynaptic $\alpha_2$-receptors. This property represents a favourable additional element in mechanism of action of the compounds according to the invention.

The above-described in vivo and isolated organ experiments confirm that, in comparison to the racemic compound of formula (3) and to other reference drugs, the substances of formulae (1) and (2) according to the invention provide considerable advantages from the viewpoint of the treatment of BPH. The low toxicity of both compounds of formulae (1) and (2) also contributes to their high therapeutic value and safety.

Thus, the invention relates also to pharmaceutical compositions useful for the treatment of benign prostatic hyperplasia, which contain the compound of formula (1) or (2), respectively, as active ingredient.

Furthermore, the invention relates to a process for the preparation of compounds of formulae (1) and (2)

The compounds of formulae (1) and (2) as well as their acid-addition salts are prepared by reacting the corresponding optically active N-([1,4]benzodioxan-2-ylmethyl)-N-(3-chloro-1-propyl)-amine of R configuration of formula (4)

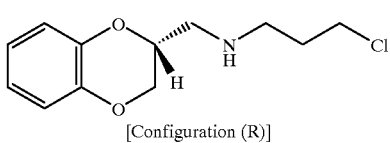

[Configuration (R)]

or S configuration of formula (5)

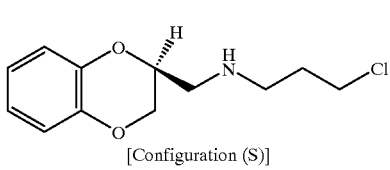

[Configuration (S)]

with 3(2H)-pyridazinone of formula (6)

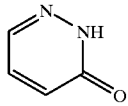
(6)

and, if desired, converting the free base obtained to an acid-addition salt.

According to a preferred embodiment of the process of invention, a salt of the compound of formula (6), optionally prepared with a base in situ, is used and the reaction is carried out in an aprotic or protic solvent at a temperature between 20° C. and 150° C.

Preferably an alkaline metal salt, e.g. potassium or sodium salt, of the compound of formula (6) is reacted with the compound of formula (4) or formula (5) in a polar or apolar aprotic solvent at a temperature between 20° C. and the boiling point of the solvent employed. Dimethyl sulfoxide, dimethyl formamide or toluene are preferable solvents for this reaction. Optionally, a catalyst, e.g. potassium or sodium iodide and/or a quaternary ammonium salt, e.g. tetrabutylammonium bromide, can be used in the reaction.

According to a particularly preferred embodiment of the process of the invention, the anhydrous potassium salt of the compound of formula (6) is reacted with the chloropropyl alkylating agent of formula (4) in order to obtain the compound of formula (1); whereas the chloropropyl alkylating agent of formula (5) is used for preparing the compound of formula (2). The reaction is carried out in dimethyl sulfoxide at room temperature for about 20 hours under stirring.

According to another advantageous embodiment of the process the above reactants are brought to interaction in toluene, in the presence of tetrabutylammonium bromide at the boiling point of the reaction mixture.

The reaction mixture may be processed in a manner known per se, e.g. in such a way that, after treatment with water and optionally, after alkalinization of the mixture, the product is extracted into a water-immiscible solvent. The crude product may be purified in its base form, e.g. by using chromatographical methods; or can be transformed to one of its acid-addition salts which may be recrystallized or, if desired, from the acid-addition salt obtained another acid-addition salt can be prepared.

3(2H)-pyridazinone or formula (6) used as starting substance in the above reaction is a known compound [see, e.g. Staehelin et al.: Helv. Chim. Acta 39, 1741 (1956)].

The optically active compounds of formulae (4) and (5) are new and also involved in the scope of the invention. These compounds can be prepared e.g. by the resolution of the racemic compound of formula (7).

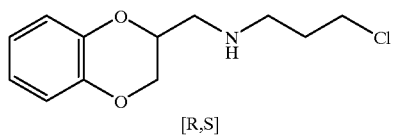
[R,S]
(7)

The compound of formula (7) can be obtained e.g. according to the German patent specification No. 1,118,218.

The resolution can be performed e.g. by preparation of the diastereomeric salts from the racemic base with an optically active acid by separating, e.g. by fractional crystallization, the diastereomeric salt pair and then, after liberating the bases from the separated diastereomeric salts, the enantiomers of formulae (4) and (5) are individually obtained. The diastereomeric salts are preferably prepared by using L(−)-dibenzoyltartaric acid. An example of resolution will be described in connection with the preparative Examples.

As mentioned above, the compounds of formulae (1) and (2) possess a valuable pharmacological action; they favourably influence the symptoms of BPH.

For therapeutic purposes, the doses of active compounds of the invention are:

in general from 0.05 mg/kg of body weight up to 2.0 mg/kg of body weight;

preferably from 0.1 mg/kg of body weight up to 0.5 mg/kg of body weight;

which are optionally divided to subdoses, by considering also the conditions of absorption. Nevertheless, doses different from the above doses may also be employed depending upon the severity of the treated clinical symptoms and with consideration of the general state of the treated patient.

For therapeutical purposes the administration can be performed e.g. in the form of tablets, pills, capsules, granules, fine powders, suppositories, ointments, aqueous or non-aqueous injections, or injectable emulsions or suspensions and the like, as well as in the form of a solid injectable composition which should be dissolved, emulsified or suspended before use. The use of pharmaceutical compositions of the invention can be effective both in oral and parenteral routes (e.g. by administration of an injectable solution in intravenous, intramuscular or subcutaneous route); or by rectal use and the like. The oral administration is usually preferred.

The pharmaceutical compositions according to the invention may contain commonly used carriers and vehicles such as sterile water, vegetable oils and the like; and may include biologically acceptable solvents, e.g. ethanol, glycerol, propylene glycol and the like; as well as fillers, adhesives, lubricating, dyeing, flavouring, emulsifying and suspending agents (e.g. Tween 80, acacia gum and the like); as well as other additives.

The invention is illustrated in detail by the following non-limiting Examples.

The chemical and optical purity of the compounds were established by using high pressure liquid chromatography (HPLC).

Examination of the chemical purity: Nucleosil $C_{19}$ column; mobile phase: $KH_2PO_4$ phosphate buffer/Na lauryl sulfate/acetonitrile.

Examination of the optical purity: Chiral-AGP column; phosphate buffer/acetonitrile.

Melting points were taken on a Boëtius type melting point apparatus.

EXAMPLE 1

R-2-[3-([1,4]Benzodioxan-2-ylmethylamino)-1-propyl]-3(2H)-pyridazinone hydrochloride After portionwise adding 1.40 g (29.2 mmol) of 50% sodium hydride to 57 ml of anhydrous dimethyl sulfoxide under nitrogen while stirring, the suspension is stirred at room temperature for 10 minutes. Then, after adding 2.80 g (9.2 mmol) of 3(2H)-pyridazinone, a solution containing 7.00 g (29.0 mmol) of R—N-([1,4]benzodioxan-2-ylmethyl)-N-(3-chloro-1-propyl)amine in 11 ml of dimethyl sulfoxide is dropped to within 10 minutes. The reaction mixture is stirred at room temperature for about 4 hours and let to stand overnight. Subsequently, it is poured into 50 ml of ice-water and extracted four times with 10 ml of toluene each. After clarifying the organic phases with activated carbon and then extracting them twice with 50 ml of 1 N hydrochloric acid each, the combined aqueous-acidic phase is washed with toluene. After making the aqueous phase alkaline by adding 35% sodium hydroxide solution up to pH 9 under cooling by ice, it is extracted 5 times with 20 ml of methylene chloride each, then the combined organic phase is dried over anhydrous potassium carbonate. The residue obtained after filtration and evaporation of the solvent is purified by chromatography on a silica gel column. The elution is performed with a mixture of acetone and toluene.

After dissolving the crude base obtained in a mixture of 6 ml of ethanol and 14 ml of ethyl ether, the solution is acidified until pH 5 by adding 20% ethanolic hydrogen chloride solution at −5° C. The reaction mixture is stirred for one hour at −5° C., then the precipitate is filtered, washed with ether and dried to give the title hydrochloride in a yield of 3.0 g (31%), m.p.: 151–152° C.

Optical activity: $[\alpha]_D^{18}$=+50.3° (c=1, ethanol)

Chemical and optical purity as determined by HPLC method: ≧99.5%.

EXAMPLE 2

S-2-[3-([1,4]Benzodioxan-2-ylmethylamino)-1-propyl]-3(2H)-pyridazinone hydrochloride The process described in Example 1 is followed, except that S—N-([1,4]benzodioxan-2-ylmethyl)-N-(3-chloro--1-propyl)amine is used instead of R—N([1,4]benzodioxan-2-ylmethyl)-N-(3-chloro-1-propyl)amine to obtain the title hydrochloride in a yield or 3.2 g (33%), m.p.: 152–153° C.

Optical activity: $[\alpha]_D^{18}$=−50.8° (c=1, ethanol)

Chemical and optical purity as determined by HPLC method: ≧99.5%.

R- and S—N-([1,4]benzodioxan-2-ylmethyl)-N-(3-chloro-1-propyl)amine used as starting materials in Example 1 and 2, respectively, can be prepared e.g. as follows.

To a solution containing 12.0 g (50.0 mmol) of racemic N-([1,4]benzodioxan-2-ylmethyl)-N-(3-chloro-1-propyl) amine base (liberated from its hydrochloride salt by adding 35% sodium hydroxide solution) in 97 ml of acetone, 18.85 g (50.0 mmol) of L(−)-dibenzoyltartaric acid monohydrate are added under stirring. The solution is stirred at room temperature for 4 hours, then let to stand overnight. The precipitate is collected by filtration and recrystallized several times from acetone.

Thus, the L(−)-dibenzoyltartarate salt of R—N-([1,4] benzodioxan-2-ylmethyl)-N-(3-chloro-1-propyl)amine is obtained with 1:1 stoichiometric composition in a yield of 4.5 g (30%), m.p.: 149–150° C.

After evaporating the above filtrate under reduced pressure, the base [containing S—N-([1,4]benzodioxan-2-ylmethyl)-N-(3-chloro-1-propyl)amine as main component] is separated from the evaporation residue [which is a mixture rich in S—N-([1,4]benzodioxan-2-ylmethyl)-N-(3-chloro-1-propyl)amine salt] by adding 35% sodium hydroxide solution. The pure amine salt of (S) configuration is obtained from the base prepared as follows:

To the solution of 7.1 g (30.0 mmol) of crude base in 15 ml of ethanol, 5.65 g (15.0 mmol) of L(−)-dibenzoyltartaric acid monohydrate are added. After stirring the reaction mixture at room temperature for 2 hours, the precipitate is filtered, recrystallized from ethanol several times and dried.

Thus, the L(−)-dibenzoyltartarate salt of S—N-([1,4] benzodioxan-2-ylmethyl)-N-(3-chloro-1-propyl)amine is obtained with 2:1 stoichiometric composition in a yield of 4.2 g (33%), m.p.: 100–101° C.

The chemical and optical purity of both diastereomeric salts are ≧99% based on HPLC analysis.

The amine bases of R and S configuration are liberated by adding 35% sodium hydroxide solution to the diastereomeric salts in water, and used directly for the preparation of the compounds of Examples 1 and 2, respectively.

Pharmacological Studies

Effect on the intraurethral and diastolic blood pressure on anaesthetized cats

This investigation was performed according to the method of Lefèvre et al. [Br. J. Pharmacol. 109, 1282 (1993)]. The essence of the method can be summarized as follows.

Cannules were introduced into the femoral artery and vein of pentobarbitone-anaesthetized, artificially ventilated cats of both sexes weighing 2.5 to 3.5 kg for administration of the compounds and measurement of blood pressure. The bladder was exposed by lower median laporotomy and a catheter was introduced into the urethra through the trigonum. The arterial and intraurethral pressures were registered on a Hellige polygraph by using a pressure transducer.

For excluding autonomic effects mediated not through $\alpha$-adrenoceptors, mecamylamine, atropine and propranolol were administered intravenously in doses of 0.5, 0.75 and 0.5 mg/kg, respectively.

An increase in intraurethral and blood pressure was induced by phenylephrine infusion of 15 $\mu$g/kg/min; the change over the baseline pressure was considered to be 100%. The test substances were administered intravenously in 1–1000 $\mu$g/kg cumulative bolus doses. An interval of at least 5 minutes was allowed after each dose. The dose of $\alpha$-antagonist inhibiting by 50% the phenylephrine-induced increase in urethral pressure ($ED_{50}$ urethra) as well as the dose decreasing by 50% the phenylephrine-induced diastolic total pressure elevation ($ED_{50}$ diastolic value) were determined.

$\alpha_1$-Adrenoceptor antagonistic effect in isolated organ experiments

A) Investigation of postsynaptic $\alpha_1$-adrenoceptors or the rat mesenteric artery This test was performed according to the method of Angus et al. [J. Physiol. 403, 495 (1988)]. The upper mesenteric artery preparation was suspended in Krebs solution bubbled with carbogen at 37° C. A pre-tension of 1 g and an equilibration period of 1.5 hour were used. A cumulative dose/effect curve was established for phenylephrine. Then, after two washings and a 30-minute incubation with the antagonist, the dose/effect curve was repeatedly determined. For characterizing the antagonistic effects, $pA_2$ values were calculated.

B) Investigation of postsynaptic $\alpha_1$-adrenoceptors on human prostate preparation This test was performed according to the method of Scheu-Eei Yu et al. (Eur. J. Pharmacol. 252, 29 (1994)].

Strips prepared from human hyperplasic prostate tissue were suspended in a Krebs solution bubbled with carbogen at 37° C. A pre-tension of 1 g and an equilibration period of 1 hour were used. A dose/effect curve was established for phenylephrine. Then, after washing out and incubation with the antagonist for 30 minutes, the dose/effect curve was again determined. For characterizing the antagonistic effects, $pA_2$ varies were calculated.

Pre- and postsynaptic $\alpha_2$-adrenoceptor antagonistic effects

A) Presynaptic $\alpha_2$-adrenoceptor antagonism on the rat vas deferens preparation Briefly, the experiment was performed as follows.

Vasa deferents were isolated from SPRD rats according to Vizi et al. [N. S. Arch. Pharmacol. 280, 79 (1973)]. The preparation was suspended in a Krebs solution at 35° C. and stimulated electrically.

A dose/effect curve was determined for xylazine. Then, after washing out, the organ was incubated with the antagonist. The dose/effect curve was taken again with xylazine in the presence of the antagonist. The antagonism was characterized by the $pA_2$ value determined according to the method of Arunlakshana and Schield [Br. J. Pharmacol. 14, 48 (1959)].

B) Postsynaptic $\alpha_2$-adrenoceptor antagonism in dog vena saphena preparation This investigation was carried out by the method of Fowler et al. [J. Pharmacol. Exp. Ther. 229, 712 (1984)] with slight modification.

$\beta$-Adrenoceptors were inactivated with propranolol. A cumulative dose/effect curve was established for the selective $\alpha_2$-adrenoceptor agonistic compound UK 14304. After 30 minutes, the organs were incubated with the agonist for 30 minutes. Also here, the antagonism was characterized by the $pA_2$ values.

What is claimed is:

1. R—N-([1,4]benzodioxan-2-ylmethyl)-N-(3-chloro-1-propyl)-amine of the formula (4) which is essentially free of its (S) stereoisomer, or a dibenzoyltartrate salt of (4).

2. S—N-([1,4]benzodioxan-2-ylmethyl)-N-(3-chloro-1-propyl)-amine of the formula (5) which is essentially free of its (R) stereoisomer, or a dibenzoyltartrate salt of (5).

3. The R—N-([1,4]benzodioxan-2-ylmethyl)-N-(3-chloro-1-propyl)amine defined in claim 1 having optical purity of at least 99% or its dibenzoyltartrate salt.

4. The S—N-([1,4]benzodioxan-2-ylmethyl)-N-(3-chloro-1-propyl)amine defined in claim 2 having optical purity of at least 99% or its dibenzoyltartrate salt.

* * * * *